United States Patent
Nakata et al.

(10) Patent No.: US 6,984,629 B2
(45) Date of Patent: Jan. 10, 2006

(54) ECTOCORNEA EXTENSION PROMOTERS

(75) Inventors: Katsuhiko Nakata, Sakurai (JP); Masatsugu Nakamura, Nara (JP); Tsutomu Fujihara, Kadoma (JP); Hiromi Fujita, Osaka (JP)

(73) Assignees: Santen Pharmaceutical Co., Ltd., Osaka (JP); Inspire Pharmaceuticals, Inc., Durham, NC (US)

( * ) Notice: Subject to any disclaimer, the term of this patent is extended or adjusted under 35 U.S.C. 154(b) by 59 days.

(21) Appl. No.: 10/297,233

(22) PCT Filed: May 30, 2001

(86) PCT No.: PCT/JP01/04520

§ 371 (c)(1), (2), (4) Date: May 20, 2003

(87) PCT Pub. No.: WO01/91795

PCT Pub. Date: Dec. 6, 2001

(65) Prior Publication Data

US 2003/0186927 A1 Oct. 2, 2003

(30) Foreign Application Priority Data

May 30, 2000 (JP) .............................. 2000-159889

(51) Int. Cl.
*A61K 31/70* (2006.01)
(52) U.S. Cl. ..................... 514/47; 514/51; 514/912
(58) Field of Classification Search ................. 514/47, 514/51, 912
See application file for complete search history.

(56) References Cited

FOREIGN PATENT DOCUMENTS

| WO | WO 98/34942 A2 | 8/1998 |
| WO | WO 99/61012 A2 | 12/1999 |
| WO | WO 00/50024 A2 | 8/2000 |
| WO | PCT/JP01/04520 | 8/2001 |

OTHER PUBLICATIONS

Kimura K. et. al., Effects of ATP and its analogues on (Ca2 + dynamics in the rabbit cornealepithelium., Archives of Histology and Cytology, May 1999, vol. 62, No. 2, p. 129-38, whole document, especially Summary).*

Cha Seok Ho et. al., Purinoceptor-Medicated Calcium Mobilization and Cellular Proliferation in Cultured Bovine Corneal Endothelial Cells, *Japanese Journal of Pharmacology*, Mar. 2000, vol. 82, 181-187, whole document, especially Abstract, Fig. 6 and Discussion.

Kimura K. et. al., Effects of ATP and its analogues on [Ca2+]i dynamics in the rabbit corneal epithelium, *Archives of Histology and Cytology*, May 1999, vol. 62, No. 2, p. 129-38, whole document, especially summary.

\* cited by examiner

*Primary Examiner*—James O. Wilson
*Assistant Examiner*—Howard V. Owens, Jr.
(74) *Attorney, Agent, or Firm*—Howrey LLP; Viola T. King

(57) ABSTRACT

Based on research for compounds that can display a corneal epithelial migration promoting effect in ophthalmology, the present invention provides P2Y receptor agonist corneal epithelial migration promoters, such as phosphoric acid compounds having an adenosyl group, uridyl group, xanthosyl group, guanosyl group, or thymidyl group, or their salts, with excellent corneal epithelial migration promoting effects.

15 Claims, No Drawings

ECTOCORNEA EXTENSION PROMOTERS

This application is a National Stage of International Application PCT/JP01/04520, filed May 30, 2001; which claims the priority of JP 2000-159889, filed May 30, 2000.

TECHNICAL FIELD

The present invention pertains to a type of corneal epithelial migration promoter that contains P2Y receptor agonist as the effective component.

BACKGROUND

The cornea is transparent tissue with no blood vessels, a diameter of about 1 cm and a thickness of about 1 mm. The transparency of a cornea has an important influence on visual function. Various physiological and biochemical phenomena of the cornea mainly function to maintain this transparency.

Corneal epithelial defects caused by corneal ulcers, exfoliation of corneal epithelium, keratitis, dry eyes, and various other diseases can be repaired naturally if no mixed infection occurs. However, if repair is delayed or not made for certain reasons, corneal epithelial migration takes place, such that the normal epithelium construction is adversely affected, and the structure and function of the parenchyma and endothelium are also harmed. In prior art, the principal therapy was the so-called passive method, in which the surface of the cornea is protected from external stimulation so that the epithelium again extends naturally to cover the damaged portion. In recent years, with developments in cell biology, factors pertaining to split, movement, fusion, migration, etc., have been clarified, and it has been reported that compounds that can promote corneal epithelial migration play an important role (Ringan, 46, 738–743 (1992); Ganka Shujutsu, 5, 719–727 (1992)).

On the other hand, many authors have reported research on P2Y receptor agonists which are the effective component in the present invention. For example, U.S. Pat. No. 5,292,498 described use of uridine 5'-triphosphate (UTP), adenosine triphosphate (ATP), etc., in maintaining secretion of mucus as a characteristic feature in treating lung diseases. WO 97/29756 stated that UTP or other phosphoric acid nucleoside P2Y receptor agonists are effective in treating tympanitis. WO 98/34593 stated that UTP or other P2Y receptor agonists have a tear secreting function, and can be used in treating dry eyes and diseases of the nasolacrimal duct. However, no research yet exists on the corneal epithelial migration effect of P2Y receptor agonists.

Discovery of new applications of said P2Y receptor agonists is of great interest. Also, in ophthalmology, searching for compounds that can display a corneal epithelial migration promoting effect is a very important topic.

DISCLOSURE OF THE INVENTION

The present inventors have searched for various compounds and performed tests on their pharmacological functions, and have found that P2Y receptor agonists have a corneal epithelial migration promoting effect. As a result, the present invention was reached.

The present invention provides a type of corneal epithelial migration promoter which contains as its effective component a P2Y receptor agonist; that is, a compound represented by following formula [I] (hereinafter referred to as "these compounds" if not specified otherwise).

The present invention also provides a corneal epithelial migration promoting method characterized by the fact that the patient is administered a composition containing an effective amount of a P2Y receptor agonist or a pharmacologically tolerated salt of it together with pharmacologically tolerated additives.

The present invention also pertains to the use of P2Y receptor agonists for manufacturing a corneal epithelial migration promoter.

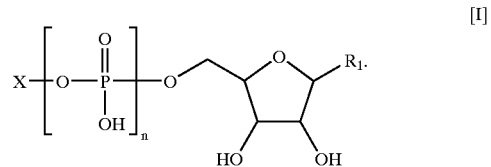

[I]

(where, n represents an integer of 1–4; X represents a hydrogen atom or the following group represented by formula [II]:

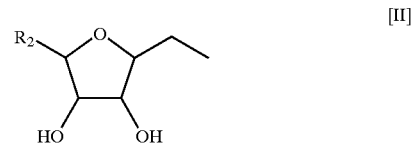

[II]

where $R_1$ and $R_2$, which may be identical or different from each other, represent a uracil group, thymine group, adenine group, hypoxanthine group, or guanine group).

In these compounds, the uracil group, thymine group, adenine group, hypoxanthine group, and guanine group are optionally substituted with the following groups: a halogen atom such as fluorine, chlorine, and bromine, methyl group, ethyl group, propyl group, hexyl group, and $C_{1-6}$ straight-chain or branched lower alkyl groups, methoxy group, ethoxy group, propyloxy group, hexyloxy group, and other $C_{1-6}$ straight-chain or branched lower alkoxy groups, phenyl group, tolyl group, and other aryl groups, phenoxy group, and other aryloxy groups, benzyl group, phenethyl group, and other aralkyl groups, hydroxyl group, etc. Also, amino groups in the adenine group or guanidine group may be protected with generally used protecting groups. Examples of protecting groups include an acetyl group, pivaloyl group, and other $C_{2-6}$ lower alkanoyl groups, a benzoyl group, and other arylcarbonyl groups. Examples of preferable groups of $R_1$ and $R_2$ include the adenine group and uracil group.

There is no special limitation on the salts of these compounds, as long as they are tolerated pharmaceutically. Examples of salts that may be used include salts of sodium, potassium, calcium, and other alkali metals or alkaline earth metals; salts of ammonia or diethylamine, triethanolamine, and other organic amines; salts of hydrochloric acid, sulfuric acid, phosphoric acid, and other inorganic acids; salts of lactic acid, maleic acid, fumaric acid, oxalic acid, methanesulfonic acid, para-toluenesulfonic acid, and other organic acids; etc.

Among these compounds, there are optical isomers and diastereo isomers. These isomers are also included in the present invention. Also, these compounds may be in the form of a hydrate or other solvates.

Examples of compounds having particularly excellent effects include uracil 5'-diphosphoric acid, adenosine 5'-diphosphoric acid, uridine 5'-triphosphoric acid, adenosine 5'-triphosphoric acid, and $P^1$, $P^4$-di(uridine-5')tetraphosphoric acid represented by formula [III], or their salts.

The concentration of P2Y receptor agonist in eye drops is selected corresponding to symptoms, age, etc., and there is no special limitation on it. Usually, however, the concentration should be in the range of 0.0001%–15%, or preferably in the range of 0.01%–10%. The dose of eye drops is in the range of one drop—several drops for each round of administration, and one—several rounds a day. In addition to conventional eye drops, the form of preparation of the eye drops may also be such that the agonist is dissolved just before use. Also, the form of preparation may be an eye ointment.

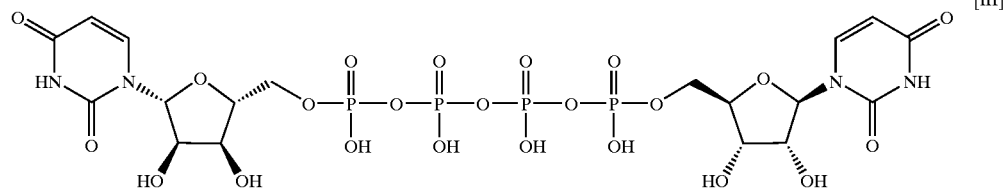

[III]

Among these compounds, the sodium salt represented by formula [IV] in particular, displays an excellent corneal epithelial migration promoting effect.

When the formulation is prepared it is possible to add various additives, as needed, such as sodium chloride, potassium chloride, or other isotonic agents, sodium phos-

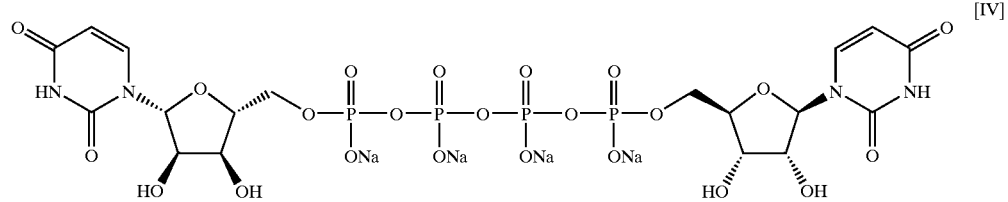

[IV]

As pointed out in the prior art section, repair of a cornea that was damaged for various reasons is closely related to corneal epithelial migration. As proved in the pharmacological tests to be described later, P2Y receptor agonists of the present invention display excellent corneal epithelial migration promoting effects. Consequently, they may be used in treating various corneal diseases. Examples of corneal diseases include corneal ulcers, exfoliation of corneal epithelium, keratitis, etc. Also, since no substantial difference has been observed between corneas and conjunctiva, P2Y receptor agonists can display repair effects not only for corneas, but also for diseases of conjunctiva. In summary, P2Y receptor agonists are useful in treating diseases of corneas and conjunctiva.

Among the several sub-types of P2Y receptors, $P2Y_2$ receptors are particularly good. Typical compounds of $P2Y_2$ receptor agonists are disclosed in U.S. Pat. No. 5,292,498, WO 97/29756, etc.

There is no special limitation on the method of administration of a P2Y receptor agonist in the present invention. However, it is preferred that a P2Y receptor agonist be administered by local administration; in particular, as eye drops.

phate, sodium hydrogen phosphate, sodium dihydrogen phosphate, or other buffers, sodium edetate or other stabilizers, benzalconium chloride, sorbic acid, or other preservatives, sodium hydroxide, dilute hydrochloric acid, or other pH adjustors, white Vaseline, fluidic paraffin, or other base agents for eye ointments. The formulation is prepared using a conventional method.

In the following, the present invention will be explained in detail with reference to application examples. However, these examples are only to help understand the present invention. They do not limit the range of the present invention.

OPTIMUM EMBODIMENT OF THE PRESENT INVENTION

Pharmacological Tests

Using cornea specimens collected from male Japanese white rabbits, the corneal epithelial migration length was used as an index in studying the cornea tissue culturing system according to the method of Nishida, et al. (J. Cell Biol., 97, 1653–1657 (1983)).

Experimental Method

Cornea blocks (6 specimens for each group) cut from rabbit cornea pieces were cultured in a culture solution (TCM-199) containing an invention compound at 37.5° C. and 5% $CO_2$ for 24 h. After culturing, the cornea blocks were fixed in an ethanol/glacial acetic acid (95:5 by volume) mixture solution, followed by embedding with paraffin to form slices. After removal of the paraffin, the slices were subjected to hematoxylin-eosin staining, and the length of migration of the corneal epithelial layer was observed using a microscope. As a control, culturing was also performed using a culture solution not containing an invention compound.

Results

Table 1 lists the results of corneal epithelial migration rates under action of the following compounds, with a control set at 100%: $P^1$, $P^4$-di(uridine-5')tetraphosphate tetra-sodium [DUTP-Na], uridine 5'-diphosphate di-sodium [UDP-Na], adenosine 5'-diphosphate di-sodium [ADP-Na], uridine 5'-triphosphate tri-sodium [UTP-Na], and adenosine 5'-triphosphate tri-sodium [ATP-Na].

TABLE 1

| Compound (Concentration) | Corneal Epithelial Migration Rate (%) |
|---|---|
| DUTP-Na (100 μM) | 118.9 |
| UDP-Na (100 μM) | 115.3 |
| ADP-Na (10 μM) | 116.1 |
| UTP-Na (100 μM) | 123.1 |
| ATP-Na (10 μM) | 119.3 |
| Control | 100.0 |

EXAMPLE FORMULATIONS

Typical formulations were prepared using $P^1$, $P^4$-di(uridine-5')tetraphosphate tetra-sodium [DUTP-Na], uridine 5'-triphosphate tri-sodium [UTP-Na], and uridine 5'-diphosphate di-sodium [UDP-Na]. Eye drops were prepared according to the following examples.

Example 1

In 100 ml:

DUTP-Na: 10 mg

Sodium chloride: 900 mg

Sterilized purified water: appropriate amount

By changing the amount of $P^1$, $P^4$-di(uridine-5')tetraphosphate tetra-sodium [DUTP-Na], eye drop concentrations of 0.03% (w/v), 0.1% (w/v), 0.3% (w/v), 1.0% (w/v), and 3.0% (w/v), were obtained.

Example 2

In 100 ml:

UTP-Na: 100 mg

Sodium chloride: 800 mg

Di-sodium hydrogen phosphate: 100 mg

Sodium dihydrogen phosphate: appropriate amount

Sterilized refined water: appropriate amount

By changing the amount of uridine-5' triphosphate tri-sodium [UTP-Na], eye drop concentrations of 0.3% (w/v), 0.5% (w/v), 1.5% (w/v), and 3.0% (w/v), were obtained.

Example 3

In 100 g:

DUTP-Na: 0.3 g

Fluidic paraffin: 10.0 g

White Vaseline: appropriate amount

By changing the amount of $P^1$, $P^4$-di(uridine-5')tetraphosphate tetra-sodium [DUTP-Na], eye ointment concentrations of 1% (w/v) and 3% (w/v) were obtained.

Example 4

In 100 g:

UDP-Na: 0.3 g

Fluidic paraffin: 10.0 g

White Vaseline: appropriate amount

By changing the amount of uridine-5'-diphosphoric acid di-sodium [UDP-Na], eye ointment concentrations of 1% (w/v) and 5% (w/v) were obtained.

As can be seen in Table 1, in the present invention, $P^1$, $P^4$-di(uridine-5')tetraphosphate tetra-sodium [DUTP-Na], uridine 5'-diphosphate di-sodium [UDP-Na], adenosine 5'-diphosphate di-sodium [ADP-Na], uridine 5'-triphosphate tri-sodium [UTP-Na], and adenosine 5'-triphosphate acid tri-sodium [ATP-Na] all can display significant corneal epithelial migration promoting effects. From such results of pharmacological tests, it is found that formulations containing P2Y receptor agonists in the present invention as the effective component can display an excellent corneal epithelial migration promoting effect, and can be used in treating diseases of corneas and conjunctiva.

INDUSTRIAL APPLICATION FIELD

P2Y receptor agonists can display an excellent corneal epithelial migration promoting effect, and can be used in treating diseases of corneas and conjunctiva.

What is claimed is:

1. A method of promoting epithelial migration in the cornea or conjunctiva, said method comprising:

administering to the eye of a subject in need thereof an epithelial migration promoter formulation containing a P2Y receptor agonist in an amount effective to promote epithelial migration in the cornea or conjunctiva, wherein said P2Y receptor agonist is a compound of formula I or its pharmacologically tolerated salts:

formula I

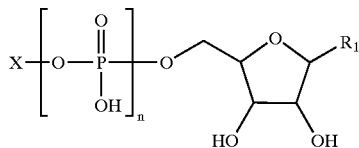

wherein n represents an integer of 1–4; X represents the following group represented by formula II:

formula [II]:

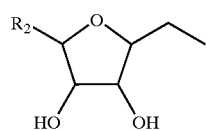

wherein $R_1$ and $R_2$ are independently a uracil group, thymine group, adenine group, hypoxanthine group, or guanine group.

2. The method according to claim 1, wherein said promoting epithelial migration is to repair epithelial defects.

3. The method according to claim 2, wherein said promoting epithelial migration to repair epithelial defects is such that the epithelium extends to cover a damaged portion of the cornea or conjunctiva.

4. The method according to claim 3, wherein said damaged portion of the cornea or conjunctiva is the result of a corneal disease.

5. The method according to claim 4, wherein said corneal disease is selected from the group consisting of corneal ulcers, exfoliation of corneal epithelium, and keratitis.

6. The method according to claim 1, wherein said epithelial migration promoter formulation contains an effective amount of said P2Y receptor agonist or its pharmacologically tolerated salt together with a pharmacologically tolerated additive.

7. The method according to claim 1, wherein said pharmacologically tolerated salts of said compound of formula I are selected from the group consisting of alkali metal salts, alkaline earth metal salts, ammonia salts, organic amine salts, hydrochloric acid salts, sulfuric acid salts, phosphoric acid salts, lactic acid salts, maleic acid salts, fumaric acid salts, oxalic acid salts, methanesulfonic acid salts, and para-toluenesulfonic acid salts.

8. The method according to claim 7, wherein said pharmacologically tolerated salts of said compound of formula I are selected from the group consisting of: sodium, potassium, calcium, ammonia, diethylamine, triethanolamine, hydrochloric acid, sulfuric acid, phosphoric acid, lactic acid, maleic acid, fumaric acid, oxalic acid, methanesulfonic acid, and para-toluenesulfonic acid salts.

9. The method according to claim 1, wherein said compound of formula I is $P^1$, $P^4$-di(uridine-5'-)tetraphosphoric acid of formula III and its salts:

formula [III]

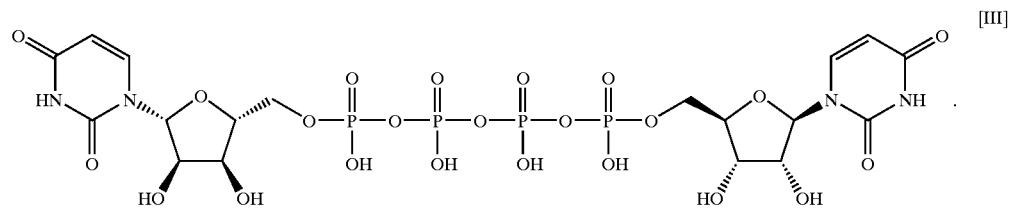

10. The method according to claim 9, wherein said compound of formula I is the sodium salt of $P^1$, $P^4$-di(uridine-5'-)tetraphosphoric acid of formula IV:

formula [IV]

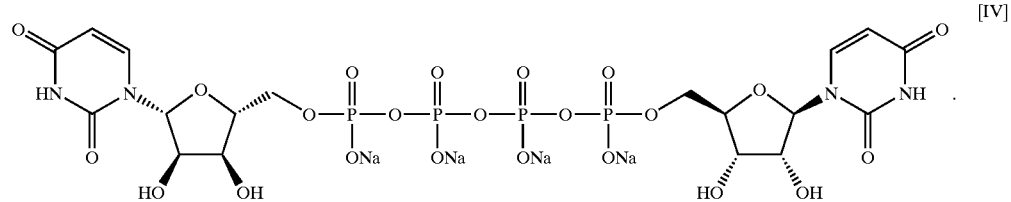

11. The method according to claim 1, wherein said amount of the P2Y receptor agonist effective to promote epithelial migration in the cornea or conjunctiva is in the range of 0.0001% to 15%.

12. The method according to claim 1, wherein said epithelial migration promoter formulation is in the form selected from the group consisting of eye drops and eye ointments.

13. The method according to claim 6, wherein said formulation contains at least one pharmacologically tolerated additive selected from the group consisting of isotonic agents, buffers, stabilizers, preservatives, pH adjustors, and base agents.

14. The method according to claim 13, wherein said additive is selected from the group consisting of: sodium chloride, potassium chloride, sodium phosphate, sodium hydrogen phosphate, sodium dihydrogen phosphate, sodium edetate, benzalconium chloride, sorbic acid, sodium hydroxide, dilute hydrochloric acid, white Vaseline, and fluidic paraffin.

15. A method of promoting epithelial migration in the cornea or conjunctiva, said method comprising:
administering to the eye of a subject in need thereof an epithelial migration promoter formulation containing a P2Y receptor agonist in an amount effective to promote epithelial migration in the cornea or conjunctiva,
wherein said P2Y receptor agonist is $P^1$, $P^4$-di(uridine 5'-)tetraphosphoric acid, or its salts.

* * * * *